United States Patent
Chiang

(10) Patent No.: US 9,352,191 B2
(45) Date of Patent: May 31, 2016

(54) SWIMMING GOGGLES

(71) Applicant: Global Esprit Inc., New Taipei (TW)

(72) Inventor: Herman Chiang, New Taipei (TW)

(73) Assignee: GLOBAL ESPRIT INC, New Taipei (TW)

( * ) Notice: Subject to any disclaimer, the term of this patent is extended or adjusted under 35 U.S.C. 154(b) by 286 days.

(21) Appl. No.: 14/055,792

(22) Filed: Oct. 16, 2013

(65) Prior Publication Data

US 2015/0089727 A1  Apr. 2, 2015

(30) Foreign Application Priority Data

Sep. 27, 2013  (TW) ............... 102218149 U

(51) Int. Cl.
*A61F 9/02* (2006.01)
*A63B 33/00* (2006.01)

(52) U.S. Cl.
CPC ............. *A63B 33/002* (2013.01); *A61F 9/02* (2013.01); *A61F 9/026* (2013.01); *A63B 2033/004* (2013.01)

(58) Field of Classification Search
CPC ......... A42B 1/04; A41D 23/00; A41D 27/00; A63B 33/002; A63B 2033/004
USPC ............. 2/426–429, 440, 445, 442; 351/43; 277/628
See application file for complete search history.

(56) References Cited

U.S. PATENT DOCUMENTS

| | | | | |
|---|---|---|---|---|
| 4,689,837 A * | 9/1987 | Bolle | ................................. | 2/440 |
| 5,093,940 A * | 3/1992 | Nishiyama | ........................ | 2/441 |
| 5,459,882 A * | 10/1995 | Yamamoto | ........................ | 2/428 |
| 5,524,300 A * | 6/1996 | Chiang | ............................ | 2/439 |
| 5,581,822 A * | 12/1996 | Tagyo | ................................ | 2/428 |
| 5,802,620 A * | 9/1998 | Chiang | ............................ | 2/428 |
| 5,890,237 A * | 4/1999 | Herman | ............................ | 2/440 |
| 5,894,606 A * | 4/1999 | Chiang | ............................ | 2/440 |
| 5,950,248 A * | 9/1999 | Kawashima et al. | ............. | 2/441 |
| 6,023,791 A * | 2/2000 | Chiang | ............................ | 2/441 |
| 6,052,834 A * | 4/2000 | Chou | ................................. | 2/428 |
| 6,098,206 A * | 8/2000 | Chou | ................................. | 2/428 |
| 6,119,277 A * | 9/2000 | Chiang | ............................ | 2/428 |
| 6,119,278 A * | 9/2000 | Kawashima | ....................... | 2/428 |
| 6,119,279 A * | 9/2000 | Haslbeck | .......................... | 2/445 |
| 6,195,807 B1 * | 3/2001 | Chou | ................................. | 2/428 |
| 6,289,523 B1 * | 9/2001 | Chiang | ............................ | 2/428 |
| 6,317,897 B1 * | 11/2001 | Chiang | ............................ | 2/428 |
| 6,321,390 B1 * | 11/2001 | Chiang | ............................ | 2/428 |
| 6,343,386 B1 * | 2/2002 | Chou | ................................. | 2/428 |
| 6,367,091 B1 * | 4/2002 | Chiang | ............................ | 2/428 |
| 6,460,196 B2 * | 10/2002 | Tsubooka et al. | ................ | 2/428 |
| 6,513,170 B1 * | 2/2003 | Chiang | ............................ | 2/428 |

(Continued)

*Primary Examiner* — Khaled Annis
(74) *Attorney, Agent, or Firm* — Cheng-Ju Chiang

(57) ABSTRACT

Swimming goggles include left and right frames each having an inner peripheral face and an outer peripheral face and being assembled with a lens, a connecting element interconnecting the left and right frames, skirt portions being respectively attached to the inner peripheral faces, and head strap apparatuses. Each of the inner peripheral faces is defined with a first arc face and a second arc face, in which the first arc face connected with the outer face, and the second arc face connected with the skirt portion. The first and second arc faces cooperatively form an angle less than 180 degrees so as to enable the skirt portions to be hermetically attached to contours of eye sockets and a nose of a wearer, whereby providing a comfortable wearing of the swimming goggles for the wearer.

9 Claims, 8 Drawing Sheets

(56) References Cited

U.S. PATENT DOCUMENTS

| | | | |
|---|---|---|---|
| 6,530,093 B1* | 3/2003 | Chiang | 2/428 |
| 6,832,394 B1* | 12/2004 | Chiang | 2/428 |
| 7,020,904 B2* | 4/2006 | Chiang | 2/442 |
| 7,143,454 B2* | 12/2006 | Kawashima et al. | 2/440 |
| 7,165,837 B2* | 1/2007 | Yokota et al. | 351/43 |
| 7,698,751 B2* | 4/2010 | Chiang | 2/450 |
| 8,122,521 B2* | 2/2012 | Chiang | 2/428 |
| 8,161,578 B1* | 4/2012 | Chou | 2/428 |
| 8,201,278 B2* | 6/2012 | Chou | 2/426 |
| 2004/0006813 A1* | 1/2004 | Chiang | 2/428 |
| 2004/0221376 A1* | 11/2004 | Kawashima et al. | 2/428 |
| 2005/0125883 A1* | 6/2005 | Fukasawa | 2/426 |
| 2005/0273915 A1* | 12/2005 | Chiang | 2/428 |
| 2008/0010728 A1* | 1/2008 | Speed | 2/426 |
| 2008/0072366 A1* | 3/2008 | Fukasawa | 2/445 |
| 2009/0064399 A1* | 3/2009 | Chou | 2/442 |
| 2010/0077538 A1* | 4/2010 | Chiang | 2/428 |
| 2010/0319112 A1* | 12/2010 | Chiang | 2/442 |
| 2011/0056003 A1* | 3/2011 | Chen | 2/440 |

\* cited by examiner

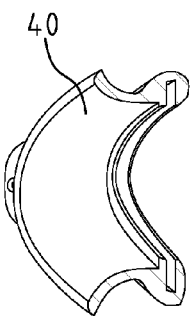 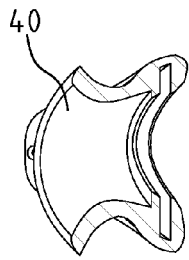 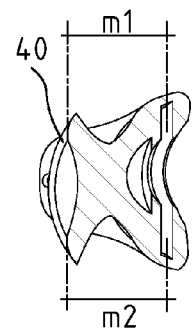 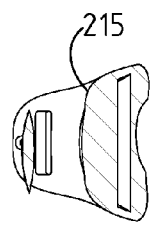
FIG.2B-D  FIG.2B-C  FIG.2B-B  FIG.2B-A
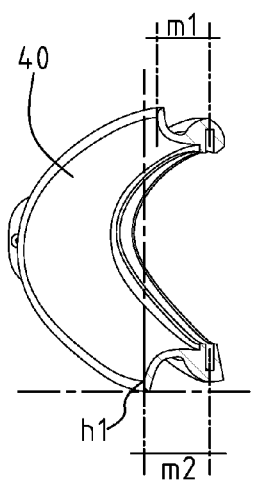 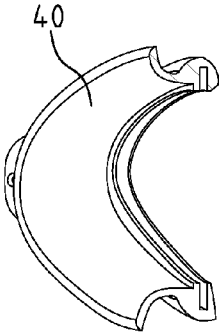 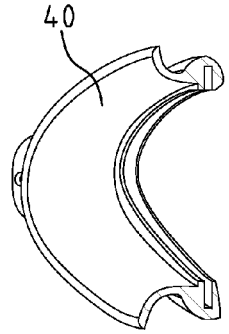 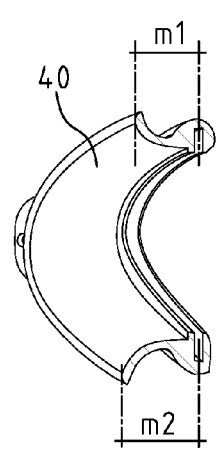
FIG.2B-H  FIG.2B-G  FIG.2B-F  FIG.2B-E

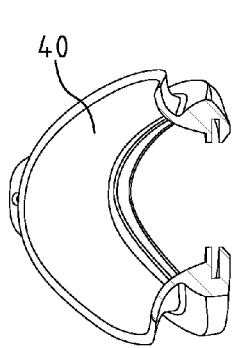 FIG.2B-L
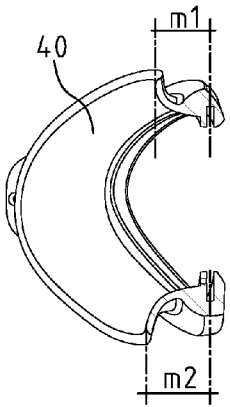 FIG.2B-K
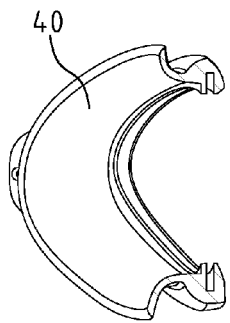 FIG.2B-J
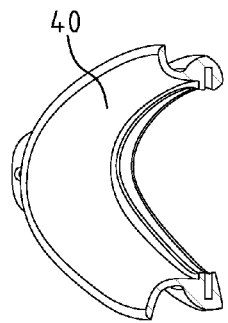 FIG.2B-I
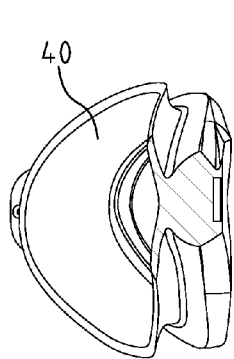 FIG.2B-P
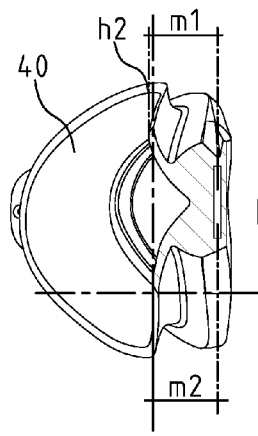 FIG.2B-O
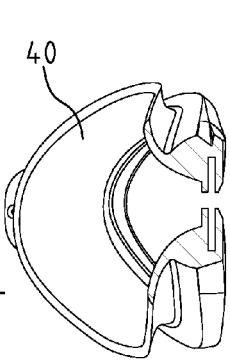 FIG.2B-N
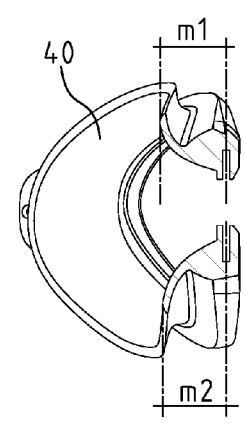 FIG.2B-M

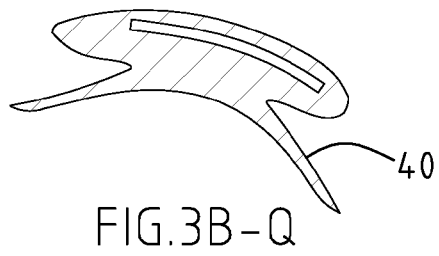
FIG.3B-Q
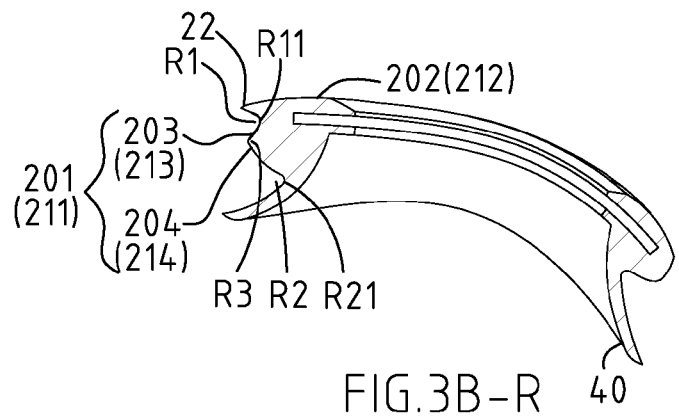
FIG.3B-R
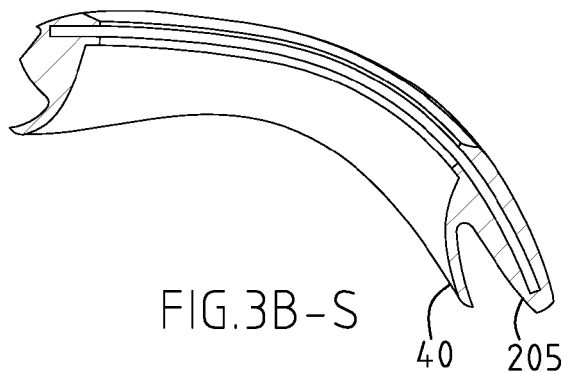
FIG.3B-S
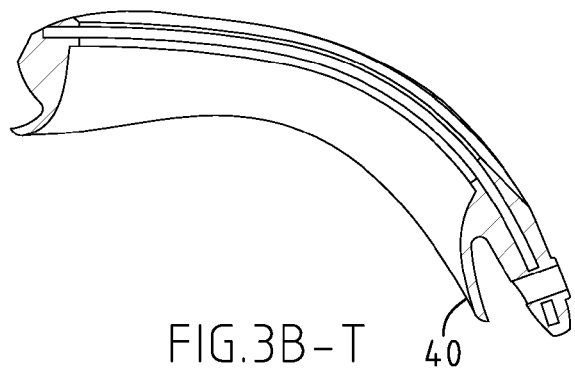
FIG.3B-T

SWIMMING GOGGLES

BACKGROUND OF THE INVENTION

1. Field of the Invention

The present invention relates to swimming goggles, and particularly to swimming goggles that are for fitting contours of eye sockets and are being worn comfortably without water leakage therein.

2. Related Art

Generally, protection pads of swimming goggles are used to provide a comfortable feeling for a wearer and to prevent water leakage into the goggles. Conventional protection pads are mainly categorized into two types: one is sponge-type protection pads, and the other one is sucker-type protection pads. The sponge-type protection pads (as shown in FIG. 7) are fixed to lens frames by adhesives; the sucker-type protection pads are manually mounted to peripheral faces of lens frames with respect to the wearer's face (as shown in FIG. 8) or are attached to the wearer's face through integral injection molding (as shown in FIG. 9). However, contours of eye sockets are irregular and ragged where in particular a portion between the eyebrow and the eye is convex, a portion between the inner eye corner and the nose is concave, a portion of the zygomatic bone near the under-eye bag is convex, and a portion near the outer can thus is concave. As a result of the irregular and ragged contours, a conventional sponge-type or sucker-type protection pad is not securely attached to the eye socket, without a sufficient force applied on the protection pad, and thus may cause water leakage into the swimming goggles. Contrarily, when the swimming goggles are being applied with an excessive force to enable the protection pads to be attached firmly, the wearer may feel uncomfortable about the eye sockets. The reason for causing the mentioned problem above, in fact, is that the sponge-type protection pads are configured to be flat with the same thickness, and the sucker-type is configured to be curved smoothly, where both types of protection pads are not completely fit for contours of eye sockets. Consequently, an excessive force is required to tighten the swimming goggles to be attached completely to the eye sockets and that makes the wearer uncomfortable and may cause red circle eyes after taking off the goggles.

SUMMARY OF THE INVENTION

Accordingly, an object of the present invention is to provide swimming goggles having skirt portions that are capable of being worn without applying excessive force thereon and are fit for contours of eye sockets, so as to provide comfortable feelings in wearing and to avoid having red circle eyes after wearing and prevent water leakage.

To achieve the above objects, the swimming goggles of the present invention comprise left and right frames each having an inner peripheral face and an outer peripheral face around the whole left and right frames and each of the left and right fames being assembled with a lens, a connecting element interconnecting the left and right frames, skirt portions respectively attached to the inner peripheral faces of the left and right frames, and head strap apparatuses; wherein each of the inner peripheral faces is defined with a first arc face and a second arc face, in which the first arc face connected with the outer face, and the second arc face connected with the skirt portion. The first and second arc faces cooperatively form an angle less than 180 degrees so as to provide a comfortable feeling in wearing.

According to one aspect of the present invention, outer peripheral edges of the first and second arc faces are not over an outer peripheral edge of the outer peripheral face, and the second arc face forms a flat surface corresponding to an outer canthus of the wearer that enables to wear the swimming goggles without applying excessive force.

According to another aspect of the present invention, the first arc face and the connecting element cooperatively form an angle less than 90 degrees at a juncture thereof, and the juncture has an arc shape which facilitates flexibility of the connecting element and allows the connecting element to fit for the contours of the nose, whereby preventing the swimming goggles from being moved in conjunction with the connecting element after being worn.

According to another aspect of the present invention, upper and lower portions of the skirt portion in a same vertical cross section have sectional widths that are either same as or different with each other in order to fit for the contours of the eye socket, and the upper and lower portions respectively have a highest edge and a lowest edge both extending radially to form the skirt portion that has a continuous curve shape so as to fit for the contours of the eye socket.

According to the above-mentioned aspect, the skirt portion in a vertical cross section taken in a middle thereof has a sectional width of the upper portion with respect to a portion above the eye less than a sectional width of the lower portion with respect to a portion below the eye, whereby enabling the lenses to be substantially parallel with the eyes and thus preventing visual fields of eye corners from being blocked by the left and right frames during swimming.

According to another aspect of the present invention, each of the outer peripheral faces of the left and right frames forms at least a flow guiding portion located below a center line of the left and right frames for effectively guiding water accumulated in a juncture of the outer peripheral face and the lens so as to avoid blocking visual fields.

According to another aspect of the present invention, the connecting element integrally interconnects the left and right frames and has an arc shape, the connecting element having front and rear ridge portions and a cross-sectional shape in a horizontal cross section that left and right ends of the front ridge portion are thinner than a portion between the left and right ends of the front ridge portion, so as to provide extensibility for the connecting element to disperse a tightening force when wearing the swimming goggles, the rear ridge portion functioning as a support structure for avoiding collapse of the connecting element, whereby to prevent the outer peripheral faces of the left and right frames from being drawn to deform and to prevent water leakage.

BRIEF DESCRIPTION OF THE DRAWINGS

FIGS. 2B-A to 2B-P are a series of cross-sectional views taken along lines from Line A-A to P-P of FIG. 2A;

FIGS. 3B-Q to 3B-T are a series of cross-sectional views taken along lines from Line Q-Q to Line T-T of FIG. 3A;

DESCRIPTION OF THE PREFERRED EMBODIMENTS

Figure 1:
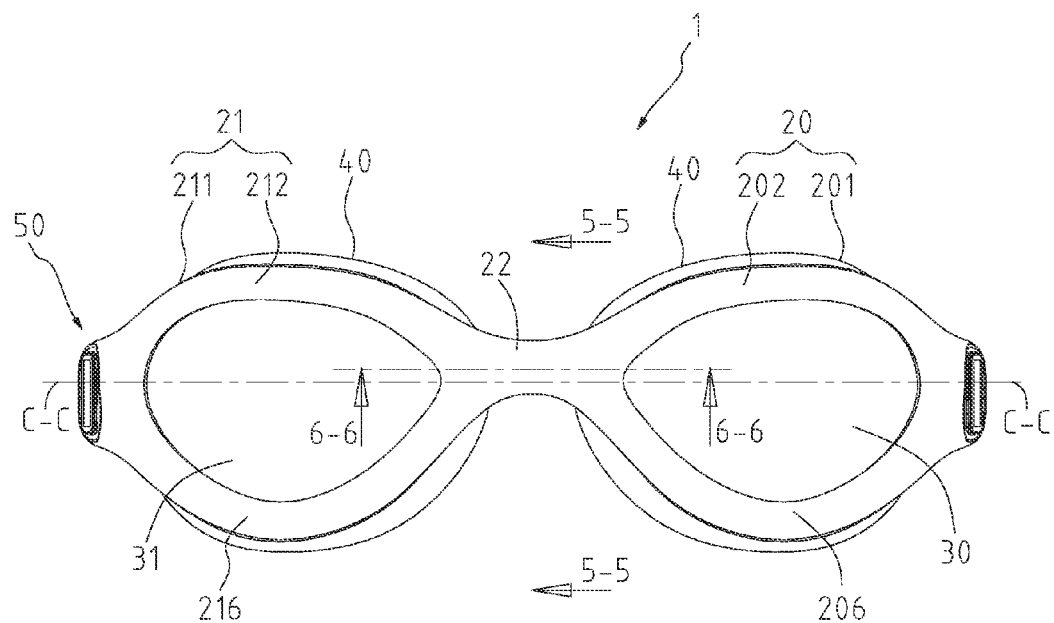
FIG. 1 is a front elevational view of swimming goggles of the present invention.

Referring to FIG. 1 showing a preferable embodiment of swimming goggles of the present invention, the swimming goggles 1 comprise a left frame 20, a right frame 21, a connecting element 22, lenses 30 and 31, skirt portions 40, and head strap apparatuses 50. The left and right frames 20 and 21 and the connecting element 22 are made of thermal plastic rubber through integral injection molding. The left and right frames 20 and 21 respectively have inner peripheral faces 201 and 211 and outer peripheral faces 202 and 212 around the whole left and right frames 20 and 21. The inner peripheral faces 201 and 211 are integrally formed with the skirt portions 40 for providing a comfortable feeling in contact with a face portion. The outer peripheral faces 202 and 212 are connected with the connecting element 22. Further referring to FIGS. 2A and 2B-A to 2B-P, and FIGS. 3A and 3B-Q to 3B-T, each of the inner peripheral faces 201 and 211 is defined with a first arc face 203 (213) and a second arc face 204 (214); outer peripheral edges of the first arc 203 (213) and the second arc face 204 (214) are not over an outer peripheral edge of the outer peripheral face 202 (212). Moreover, the second arc face 204 (214) forms a flat surface 205 (215) corresponding to an outer canthus of a wearer (as shown in Line S-S cross-sectional view in FIG. 3B-S and Line A-A cross-sectional view in FIG. 2B-A) in order to correspond to the contours of an eye socket. Particularly, the first and second arc faces 203 (213) and 204 (214) cooperatively form an angle R3 less than 180 degrees. Further referring to Line R-R cross-sectional view shown in FIG. 3B-R, the first arc face 203 (213) and the connecting element 22 cooperatively form an angle R1 less than 90 degrees at a juncture R11 thereof, wherein the juncture R11 has an arc shape which facilitates flexibility of the connecting element 22 so as to allow the connecting element 22 to be bent to fit for contours of a nose and a face, whereby preventing the swimming goggles from being moved in conjunction with the connecting element 22 after the swimming goggles have already worn to fit for the contours of the eye sockets. The second arc face 204 (214) and the skirt portion 40 cooperatively form an angle R2 less than 90 degrees at a juncture R21 thereof, wherein the juncture R21 has an arc shape, which facilitates flexibility of the skirt portion 40 and therefore allows the skirt portion 40 to flexibly smoothly bend in a direction toward the second arc face 204 (214) when being worn; thus, the skirt portion 40 functions as a sucker to reinforce ability of water leakage-proof. Referring back to FIG. 1, each of the outer peripheral faces 202 and 212 of the left and right frames 20 and 21 forms at least a flow guiding portion 206 (216) located below a center line C-C of the left and right frames 20 and 21 for effectively guiding water accumulated in a juncture of the outer peripheral face 202 (212) and the lens 30 (31) so as to avoid blocking visual fields. The flow guiding portion 206 (216) is preferably located at a middle of a lower portion of the outer peripheral face 202 (212).

The lenses 30 and 31 are made of polycarbonate resin or cellulose acetate or cellulose propionate sheet, and are respectively implanted in between the inner peripheral faces 201 and 211 the outer peripheral faces 202 and 212 prior to integral molding of the left and right frame 20 and 21 and the connecting element 22.

Figure 2A:
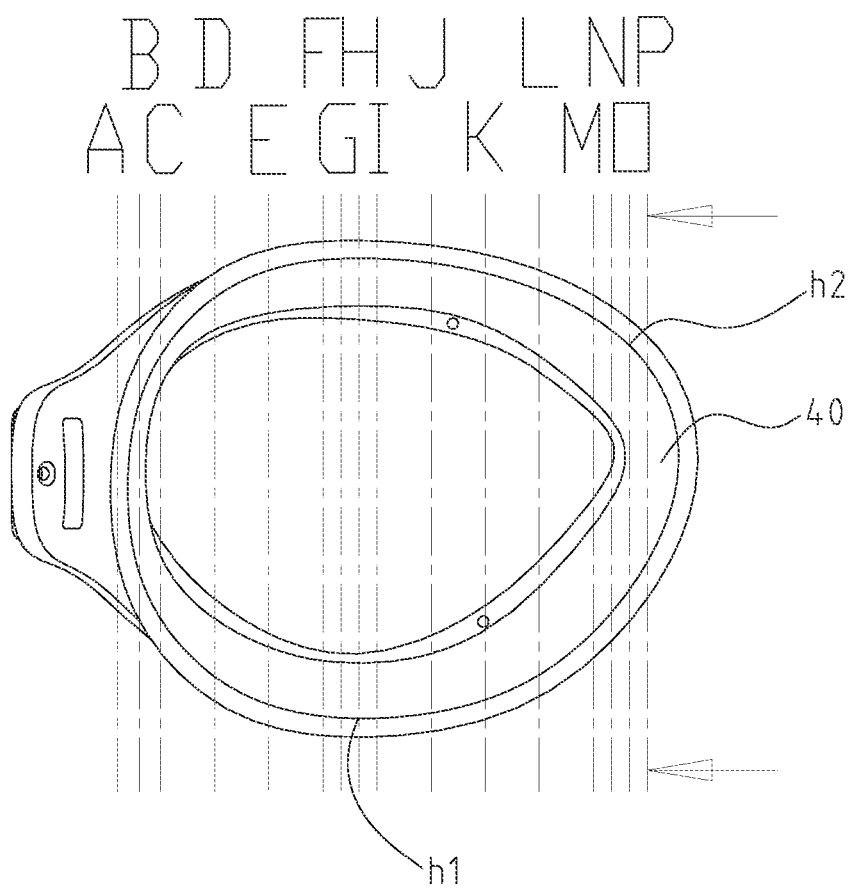
FIG. 2A is a rear elevational view of a left frame without a lens assembled therein of the swimming goggles of the present invention.
Figure 3A:
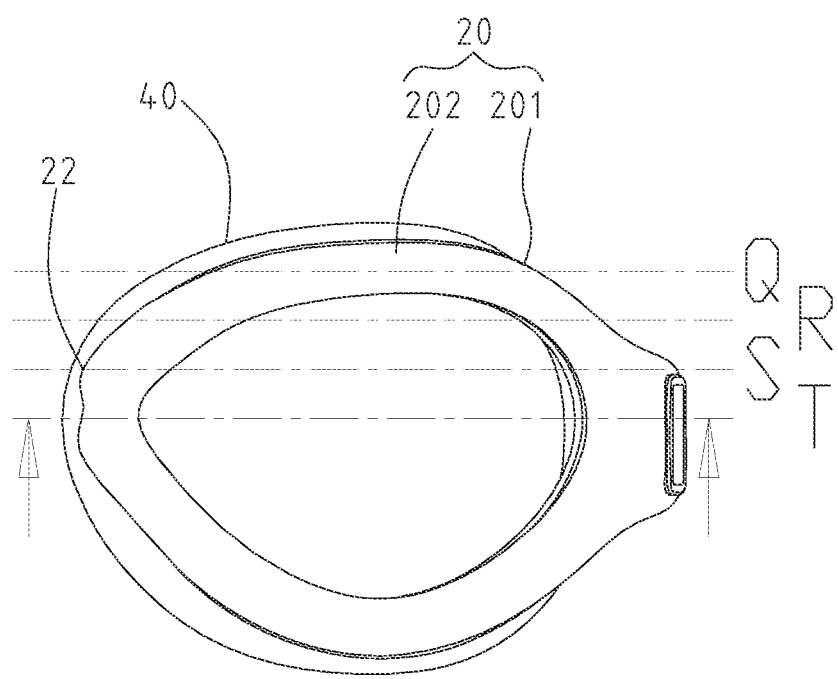
FIG. 3A is a front elevational view of the left frame without a lens assembled therein of the swimming goggles of the present invention

Referring to FIGS. 2A and 2B-A to 2B-P for the skirt portions 40, each skirt portion 40 has contours of concave and convex shapes to correspond to the eye socket. In other words, the skirt portion 40 is defined with upper and lower portions, and the upper and lower portions in a same vertical cross section have sectional widths that are either same as or different with each other in order to fit for the contours of the eye socket, wherein the sectional widths are measured from a middle of the lens 30 and 31 to the most outer edge of the skirt portion 40. For example, referring to FIG. 2B-B for a cross-sectional view taken along line B-B in FIG. 2A, a sectional width m1 at the upper portion of the skirt portion 40 is equal to a sectional width m2 at the lower portion; in FIG. 2B-E along Line E-E cross-sectional view, a sectional width m1 at the upper portion is less than a sectional width m2 at the lower portion; in FIG. 2B-K along Line K-K cross-sectional view, a sectional width m1 at the upper portion is less than a sectional width m2 at the lower portion; in FIG. 2B-M along Line M-M cross-sectional view, a sectional width m1 at the upper portion is larger than a sectional width m2 at the lower portion; and in FIG. 2B-O along Line O-O cross-sectional view, a sectional width m1 at the upper portion is larger than a sectional width m2 at the lower portion. In each of the cross-sectional views the upper and lower portions of the skirt portion 40 respectively have a highest edge and a lowest edge both extending radially to form the skirt portion 40 having a continuous curve shape so as to fit for the contours of the eye socket. Taking a cross-sectional view of the skirt portion 40 corresponding to the zygomatic bone and the under-eye bag for example by referring to an H-H cross-sectional view of FIG. 2B-H taken along line H-H in FIG. 2A, a sectional width m1 at the upper portion is less than a sectional width m2 at the lower portion; more specific, in the H-H cross-sectional view of FIG. 2B-H, the lower portion of the skirt portion 40 is corresponding to the zygomatic bone adjacent to the under-eye bag and is more projecting than the upper portion of the skirt portion 40 (compared by an oblique line shown in the H-H cross-sectional view of FIG. 2B-H), wherein a lowest edge h1 is located at the lower portion of the skirt portion 40. Further referring to FIG. 2B-O for an O-O cross-sectional view taken along line O-O in FIG. 2A, a sectional width m1 at the upper portion of the skirt portion 40 is larger than a sectional width m2 at the lower portion; more specific, in the O-O cross-sectional view of FIG. 2B-O, the upper portion of the skirt portion 40 is corresponding to a portion above an inner canthus and is more projecting than the lower portion of the skirt portion 40 (as indicated by an oblique line that inclines toward left), whereby the upper portion of the skirt portion 40 forms a highest edge h2. As a result, the highest edge h2 and the lowest edge h1 extend radially to connect each other and form a continuous curve shape so as to fit for the contours of the eye socket. Further referring to E-E and K-K cross-sectional views of FIG. 2B-E and 2B-K that are respectively taken along vertical lines E-E and K-K in FIG. 2A, a sectional width m1 at the upper portion of the skirt portion 40 relative to an area above the eye is less than a sectional width m2 at the lower portion of the skirt portion 40 relative to an area below the eye; that is, an area above the eye is more projecting than an area below the eye. With the above contours of the skirt portions 40, the lenses 30 and 31 are parallel with the eyes after being worn and therefore avoid blocking visual fields in swimming Accordingly, the contours of the skirt portions 40 of the present invention are fit for peripheral portions of the eye sockets, whereby allowing the skirt portions 40 to be comfortably completely attached to the peripheral portions of the eye sockets without applying excessive force thereon, and preventing red circle eyes and water leakage into the swimming goggles.

Figure 5:
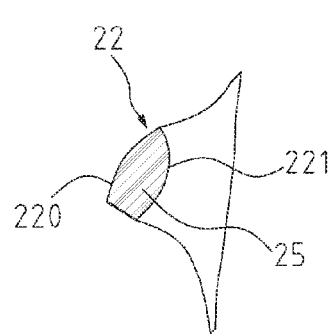
FIG. 5 is a cross-sectional view taken along line 5-5 of FIG. 1.
Figure 6:
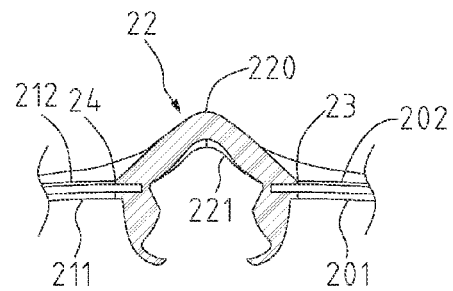
FIG. 6 is a cross-sectional view taken along line 6-6 of FIG. 1.

Referring to FIGS. 5 and 6 in combination with FIG. 1, the connecting element 22 as mentioned above is integrally formed with the left and right frames 20 and 21 and has an arc shape. The connecting element 22 has front and rear ridge portions 220 and 221 and a horizontal cross-sectional shape of which the front ridge portion is arc. In particular, left and right ends 23 and 24 of the front ridge portion 220 are thinner than a portion between the left and right ends 23 and 24, so as to provide extensibility for the connecting element 22 that is capable of dispersing a drawing force when wearing the swimming goggles and thus prevent the outer peripheral faces 202 and 212 of the left and right frames from being pulled away from the lenses 30 and 31. The rear ridge portion 221 functions as a support structure for avoiding collapse of the connecting element 22. With the above structure that the left and right ends 23 and 24 being thinner than a middle portion 25 between the left and right ends 23 and 24, a drawing force required to wear the swimming goggles is effectively buffered by the left and right ends 23 and 24, and a drawing force applied on outer sides of the left and right frames 20 and 21 are reduced, so as to prevent the outer peripheral faces 202 and 212 of the left and right frames 20 and 21 from being drawn to deform, and to prevent the swimming goggles from water leakage.

Figure 4:
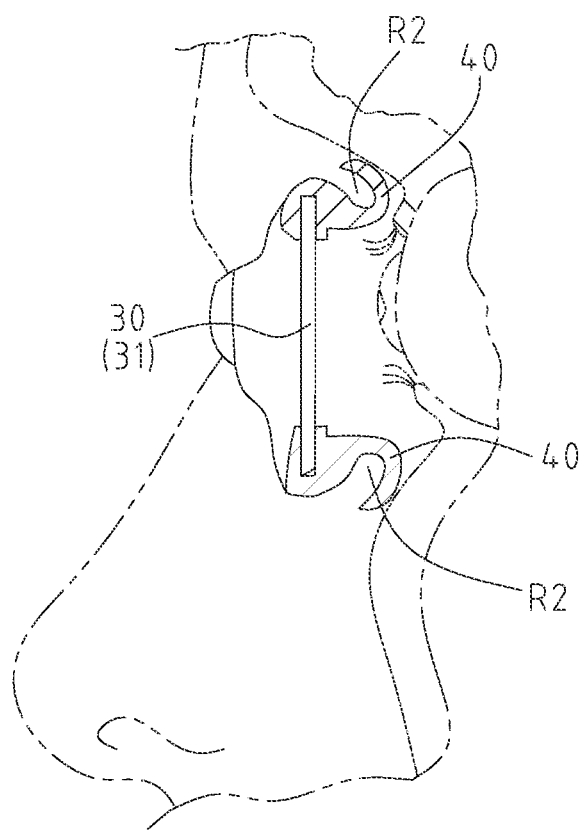
FIG. 4 is a schematic side view showing the swimming goggles being worn on a wearer's face portion.
Figure 7:
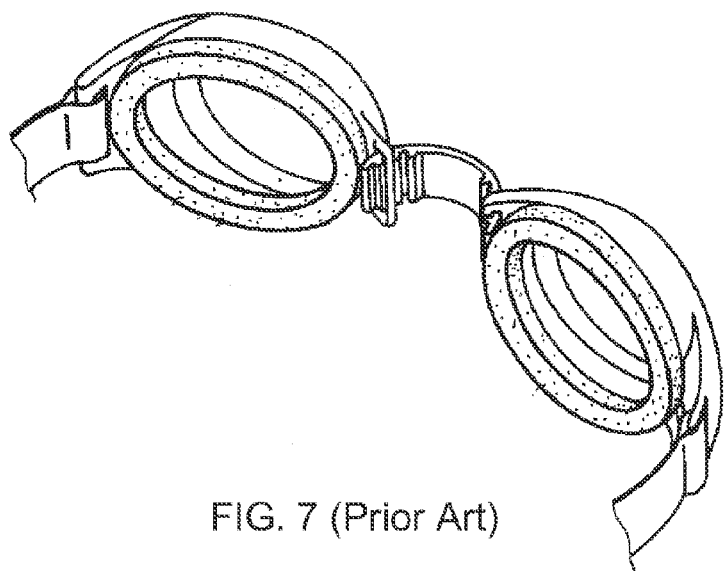
FIGS. 7-9 are schematic views of conventional swimming goggles.
Figure 8:
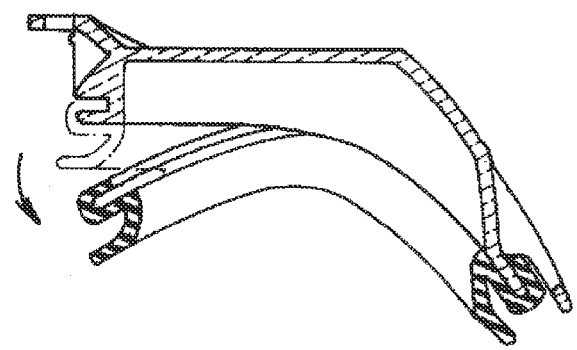
Figure 9:
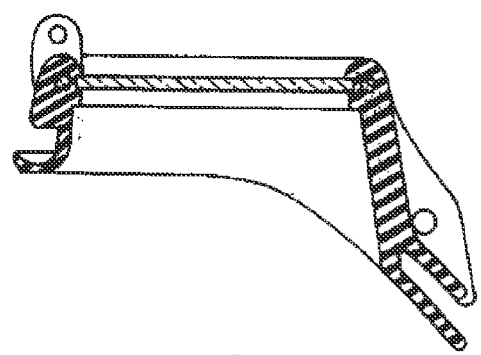

Referring to FIG. 4 in combination with FIGS. 2A and 2B-A to 2B-P, and FIGS. 3A and 3B-Q to 3B-T, the skirt portions 40 have the contours having concave and convex shapes to correspond to the eye socket, whereby providing a comfortable wearing for the wearer without exerting excessive force on wearing and preventing the swimming goggles from water leakage. Moreover, the upper and lower portions of the skirt portions 40 having different sectional widths enable the lenses 30 and 31 to remain parallel with eyes so as to avoid blocking visual fields and thus offer a better visual fields during swimming Furthermore, the at least a flow guiding portion 206 (216) located below the center line C-C of the left and right frames 20 and 21 for effectively guiding water accumulated in a juncture of the outer peripheral face 202 (212) and the lens 30 (31) so as to avoid blocking visual fields. Still further, the left and right ends 23 and 24 of the connecting element 21 being thinner than the middle portion 25 thereof effectively disperse the drawing force applied on the left and right frames 20 and 21. In sum, all the above-mentioned aspects are characters and features of the swimming goggles of the present invention.

It is understood that the invention may be embodied in other forms within the scope of the claims. Thus the present examples and embodiments are to be considered in all respects as illustrative, and not restrictive, of the invention defined by the claims.

What is claimed is:

1. Swimming goggles, comprising:
   left and right frames each having an inner peripheral face and an outer peripheral face around the entire left and right frames, and each of the left and right frames being assembled with a lens;
   a connecting element interconnecting the left and right frames;
   skirt portions respectively attached to the inner peripheral faces of the left and right frames; and
   head strap apparatuses;
   wherein each of the inner peripheral faces is defined with a first arc face and a second arc face, the first arc face connected with the outer peripheral face, the second arc face connected with the skirt portion, the first and second arc faces cooperatively forming an angle less than 180 degrees so as to enable the skirt portions to be hermetically attached for contouring eye sockets and a nose of a wearer, whereby providing a comfortable feeling during wearing;
   wherein upper and lower portions of the skirt portion in a same vertical cross section have sectional widths that have relative sizes which are variable along a horizontal direction parallel to the lens when compared to each other in order for fitting the contour of the eye sockets, and the upper and lower portions respectively have a highest edge and a lowest edge both extending radially to form the skirt portion that has a continuous curve shape adapted to fit the contour of the eye sockets;
   wherein the skirt portion in a vertical cross section taken in a middle thereof has a sectional width of the upper portion with respect to a portion above the eye sockets less than a sectional width of the lower portion with respect to a portion below the eye sockets, whereby enabling the lenses to be substantially parallel with the eye sockets and thus adapted to prevent visual fields of eye corners from being blocked by the left and right frames during swimming.

2. The swimming goggles of claim 1, wherein the second arc face forms a flat surface for corresponding to an outer canthus of the wearer, the second arc face and the skirt portion cooperatively form an angle less than 90 degrees at a juncture thereof, and the juncture has an arc shape which facilitates flexibility of the skirt portion and therefore allows the skirt portion to flexibly bend in a direction toward the second arc face when being worn, whereby the skirt portion functions as a sucker to reinforce the ability of water leakage-proof.

3. The swimming goggles of claim 1, wherein outer peripheral edges of the first and second arc faces are not over an outer peripheral edge of the outer peripheral face, the first arc face and the connecting element cooperatively form an angle less than 90 degrees at a juncture thereof, and the juncture has an arc shape which facilitates flexibility of the connecting element and allows the connecting element for fitting the contour of the nose of the wearer, whereby preventing the swimming goggles from being moved in conjunction with the connecting element when worn.

4. The swimming goggles of claim 1, wherein the sectional widths of the upper and lower portions of the skirt portion are measured from a middle of the lens to the most outer edge of the skirt portion.

5. The swimming goggles of claim 1, wherein each of the outer peripheral faces of the left and right frames forms at least a flow guiding portion located below a center line of the left and right frames for effectively guiding water accumulated in a juncture of the outer peripheral face and the lens adapted to avoid blocking visual fields.

6. The swimming goggles of claim 1, wherein the connecting element integrally interconnects the left and right frames and has an arc shape, the connecting element having front and rear ridge portions and a cross-sectional shape in a horizontal cross section that left and right ends of the front ridge portion are thinner than a portion of the front ridge portion between the left and right ends, so as to provide extensibility for the connecting element for dispersing a tightening force when wearing the swimming goggles, the rear ridge portion functioning as a support structure for avoiding collapse of the connecting element, whereby to prevent the outer peripheral faces of the left and right frames from being drawn to deform and to prevent water leakage.

7. The swimming goggles of claim 6, wherein the left and right frames, the connecting element, and the skirt portions are all made of thermal plastic rubber, and the lenses are made of polycarbonate resin, cellulose acetate or cellulose propionate sheet.

8. Swimming goggles, comprising:
left and right frames each having an inner peripheral face and an outer peripheral face around the entire left and right frames, and each of the left and right fames being assembled with a lens;
a connecting element interconnecting and integrally formed with the left and right frames;
skirt portions respectively integrally attached to the inner peripheral faces of the left and right frames; and
head strap apparatuses;
wherein upper and lower portions of each of the skirt portions in a same vertical cross section have sectional widths that have relative sizes which are variable along a horizontal direction parallel to the lens when compared to each other adapted to fit a contour of eye sockets of a wearer, and the upper and lower portions respectively have a highest edge and a lowest edge both extending radially to form the skirt portion that has a continuous curve shape adapted to fit the contour of the eye sockets, whereby enabling the skirt portions adapted to be completely attached to peripheral portions of the eye sockets without applying excessive force on the swimming goggle.

9. The swimming goggles of claim 8, wherein the sectional widths of the upper and lower portions of the skirt portion are measured from a middle of the lens to the most outer edge of the skirt portion.

* * * * *